United States Patent
Cune Castellana et al.

(10) Patent No.: US 10,265,351 B2
(45) Date of Patent: Apr. 23, 2019

(54) PROBIOTIC FOR INFANTILE COLIC

(71) Applicants: AB-BIOTICS, S.A., Cerdanyola Del Valles (ES); VENPHARMA LABORATORIOS, S.A., Barcelona (ES)

(72) Inventors: Jordi Cune Castellana, Rubi (ES); Elisabet Lazaro Mallen, Barcelona (ES); Jordi Espadaler Mazo, Girona (ES)

(73) Assignees: AB-BIOTICS, S.A., Cerdanyola Del Valles, OT (ES); VANPHARMA LABORATORIOS, S. A., Barcelona, OT (ES)

( * ) Notice: Subject to any disclaimer, the term of this patent is extended or adjusted under 35 U.S.C. 154(b) by 0 days.

(21) Appl. No.: 14/911,037

(22) PCT Filed: Aug. 7, 2014

(86) PCT No.: PCT/EP2014/066970
§ 371 (c)(1),
(2) Date: Feb. 9, 2016

(87) PCT Pub. No.: WO2015/018883
PCT Pub. Date: Feb. 12, 2015

(65) Prior Publication Data
US 2016/0184371 A1    Jun. 30, 2016

(30) Foreign Application Priority Data
Aug. 9, 2013 (EP) .................................. 13382324

(51) Int. Cl.
C12N 1/20 (2006.01)
A61K 35/744 (2015.01)
C12R 1/01 (2006.01)
A23L 33/135 (2016.01)

(52) U.S. Cl.
CPC .......... *A61K 35/744* (2013.01); *A23L 33/135* (2016.08); *C12N 1/20* (2013.01); *C12R 1/01* (2013.01); *A23Y 2280/55* (2013.01)

(58) Field of Classification Search
None
See application file for complete search history.

(56) References Cited

U.S. PATENT DOCUMENTS

| | | | |
|---|---|---|---|
| 8,021,656 B2 * | 9/2011 | Corthesy-Theulaz | A61K 35/745 424/93.45 |
| 9,340,840 B2 | 5/2016 | Connolly | |
| 2012/0058095 A1 * | 3/2012 | Strozzi | A23D 9/007 424/93.44 |
| 2012/0315249 A1 | 12/2012 | Olmstead | |

FOREIGN PATENT DOCUMENTS

| WO | 2005/077391 A1 | 8/2005 |
|---|---|---|
| WO | 2007/142596 A1 | 12/2007 |

OTHER PUBLICATIONS

Bengmark, Stig; "Synbiotic Treatment in Clinical Praxis" Host Microflora Crosstalk, Old Herborn University Seminar, 16, 69-82, 2003.*
Roberts, Donna M; et al; "Infantile Colic" American Family Physician, 70, 735-740, 2004.*
PCT/EP2014/066970., International Preliminary Report on Patentability, dated Feb. 9, 2016.
PCT/EP2014/066970., International Search Report, dated Feb. 18, 2015.
Andreoletti, O. et al. "The maintenance of the list of QPS microorganisms intentionally added to food or feed. Question No. EFSA-Q-2008-006", The EFSA Journal 2008, vol. 923, pp. 1-48.
Bosch, M. et al., "Probiotic properties of Lactobacillus plantarum CECT 7315 and CECT 7316 isolated from faeces of healthy children". Lett App. Microbiol, 2012. 54, 240-6.
Briczinski, E.P. et al. "Technical note: a rapid pulsed-field gel electrophoresis method for analysis of bifidobacteria" J. Dairy Sci. 2006, vol. 89, pp. 2424-2427.
De Weerth, C. et al. "Intestinal Microbiota of Infants with colic: Development and specific signatures" Pediatrics 2013, vol. 131, Issue 2, e550-e558.
Dupont, C. et al. "A-Lactalbumin-Enriched and Probiotic-Supplemented Infant Formula in Infants with Colic: Growth and Gastrointestinal Tolerance." European Journal of Clinical Nutrition. 2010, vol. 64, Issue 7, pp. 765-767.
Igarashi T. "Study of the relationship between changes in lactic acid bacterial cell components and stimulation of IL-12 production under salt-stressed conditions", Bioscience, Biotechnology and Biochemistry 2010, vol. 74, pp. 2171-2175.
Jonganurakkun, B. et al. "Pediococcus pentosaceus NB-17 for probiotic use", Journal of Bioscience and Bioengineering 2008 vol. 106, Issue 1, pp. 69-73.
Kruszewska D. et al.:"Selection of lactic acid 1-14 bacteria as probiotic strains", Mikrooekologie Uno Therapie,2002, vol. 29, pp. 37-49.
Lehtonen, L. et al. "Intestinal Microflora in colicky and noncolicky infants: Bacterial Cultures and Gas-Liquid Chromatography", Journal of pediatric Gastroenterology and Nutrition 1994, vol. 19, pp. 310-314.
Mentula, S. et al. "Microbial composition and fecal fermentation end products from colicky infants—A probiotic supplementation pilot", Microbial Ecology in Health and Disease, 2008, vol. 20, No. 1, pp. 37-47.

(Continued)

*Primary Examiner* — David W Berke-Schlessel
(74) *Attorney, Agent, or Firm* — Cheryl Agris; Agris & Von Natzmer, LLP

(57) ABSTRACT

Provided is a bacterial composition which comprises from $10^4$ to $10^{12}$ cfu/g of *Pediococcus pentosaceus* cells which have the ability to induce the production of interleukin-10 to reduce inflammation in the intestinal tract among other features and is useful in the amelioration of excessive crying in infants.

16 Claims, 3 Drawing Sheets

Specification includes a Sequence Listing.

(56) References Cited

OTHER PUBLICATIONS

Pilone, G.J., et al., "Characterization of wine lactic acid bacteria: single broth culture for tests of heterofermentation, mannitol from fructose, and ammonia from arginine" Am J Enol Vitic 1991, vol. 42, pp. 153-157.
Roos, S. et al. "454 Pyrosequencing Analysis on Faecal Samples from a Randomized DBPC Trial of Colicky Infants Treated with Lactobacillus reuteri DSM 17938", PLoS One 2013, vol. 8, No. 2, e56710 1-5.
Savino, F. et al. "Lactobacillus reuteri (American Type Culture Collection Strain 55730) Versus Simethicone in the Treatment of Infantile Colic: A Prospective Randomized Study" Pediatrics 2007, vol. 119, Issue 1, e124-e130.
Savino, F. et al. "Lactobacillus reuteri DSM 17938 in Infantile Colic: A Randomized, Double-Blind, Placebo-Controlled Trial." Pediatrics 2010, vol. 126, Issue 3, e526-e533.
Szajewska, H. et al. "Lactobacillus reuteri DSM 17938 for the Management of Infantile Colic in Breastfed Infants: A Randomized, Double-Blind, Placebo-Controlled Trial", Journal of Pediatrics 2012, vol. 162, Issue 2, pp. 257-262.
Vitali, B. et al. "Novel probiotic candidates for humans isolated from raw fruits and vegetables", Food Microbiology 2012, vol. 31, Issue 1, pp. 116-125.

* cited by examiner

A  Reduction in average daily crying time

B  Reduction in episode duration

SEQUENCE LISTING

```
<160> NUMBER OF SEQ ID NOS: 2

<210> SEQ ID NO 1
<211> LENGTH: 1502
<212> TYPE: DNA
<213> ORGANISM: Pediococcus pentosaceus
<220> FEATURE:
<221> NAME/KEY: source
<222> LOCATION: 1..1502
<223> OTHER INFORMATION: /mol_type="unassigned DNA"
      /note="16sRNA"
      /organism="Pediococcus pentosaceus"

<400> SEQUENCE: 1
ggatgaacgc tggcggcgtg cctaatacat gcaagtcgaa cgaacttccg ttaattgatt      60
atgacgtact tgtactgatt gagattttaa cacgaagtga gtggcgaacg ggtgagtaac     120
acgtgggtaa cctgcccaga agtaggggat aacacctgga aacagatgct aataccgtat     180
aacagagaaa accgcatggt tttcttttaa aagatggctc tgctatcact tctggatgga     240
cccgcggcgt attagctagt tggtgaggta aaggctcacc aaggcagtga tacgtagccg     300
acctgagagg gtaatcggcc acattgggac tgagacacgg cccagactcc tacgggaggc     360
agcagtaggg aatcttccac aatggacgca agtctgatgg agcaacgccg cgtgagtgaa     420
gaagggtttc ggctcgtaaa gctctgttgt taaagaagaa cgtgggtaag agtaactgtt     480
tacccagtga cggtatttaa ccagaaagcc acggctaact acgtgccagc agccgcggta     540
atacgtaggt ggcaagcgtt atccggattt attgggcgta aagcgagcgc aggcggtctt     600
ttaagtctaa tgtgaaagcc ttcggctcaa ccgaagaagt gcattggaaa ctgggagact     660
tgagtgcaga agaggacagt ggaactccat gtgtagcggt gaaatgcgta gatatatgga     720
agaacaccag tggcgaaggc ggctgtctgg tctgcaactg acgctgaggc tcgaaagcat     780
gggtagcgaa caggattaga taccctggta gtccatgccg taaacgatga ttactaagtg     840
ttggagggtt tccgcccttc agtgctgcag ctaacgcatt aagtaatccg cctggggagt     900
acgaccgcaa ggttgaaact caaaagaatt gacggggcc cgcacaagcg gtggagcatg     960
tggtttaatt cgaagctacg cgaagaacct taccaggtct tgacatcttc tgacagtcta    1020
agagattaga ggttcccttc ggggacagaa tgacaggtgg tgcatggttg tcgtcagctc    1080
gtgtcgtgag atgttgggtt aagtcccgca acgagcgcaa cccttattac tagttgccag    1140
```

| | | |
|---|---|---|
| cattaagttg ggcactctag tgagactgcc ggtgacaaac cggaggaagg tggggacgac | 1200 | |
| gtcaaatcat catgcccctt atgacctggg ctacacacgt gctacaatgg atggtacaac | 1260 | |
| gagtcgcgaa accgcgaggt taagctaatc tcttaaaacc attctcagtt cggactgtag | 1320 | |
| gctgcaactc gcctacacga agtcggaatc gctagtaatc gcggatcagc atgccgcggt | 1380 | |
| gaatacgttc ccgggccttg tacacaccgc ccgtcacacc atgagagttt gtaacaccca | 1440 | |
| aagccggtgg ggtaaccttt taggagctag ccgtctaagg tgggacagat gattagggtg | 1500 | |
| aa | 1502 | |

<210> SEQ ID NO 2
<211> LENGTH: 1461
<212> TYPE: DNA
<213> ORGANISM: Bifidobacterium longum
<220> FEATURE:
<221> NAME/KEY: source
<222> LOCATION: 1..1461
<223> OTHER INFORMATION: /mol_type="unassigned DNA"
    /note="16sRNA"
    /organism="Bifidobacterium longum"

<400> SEQUENCE: 2

| | | |
|---|---|---|
| tggctcagga tgaacgctgg cggcgtgctt aacacatgca agtcgaacgg gatccatcag | 60 | |
| gctttgcttg gtggtgagag tggcgaacgg gtgagtaatg cgtgaccgac ctgccccata | 120 | |
| caccggaata gctcctggaa acgggtggta atgccggatg ctccagttga tcgcatggtc | 180 | |
| ttctgggaaa gctttcgcgg tatgggatgg ggtcgcgtcc tatcagcttg acggcggggt | 240 | |
| aacggcccac cgtggcttcg acgggtagcc ggcctgagag ggcgaccggc cacattggga | 300 | |
| ctgagatacg gcccagactc ctacggggagg cagcagtggg gaatattgca caatgggcgc | 360 | |
| aagcctgatg cagcgacgcc gcgtgaggga tggaggcctt cgggttgtaa acctctttta | 420 | |
| tcggggagca agcgagagtg agtttacccg ttgaataagc accggctaac tacgtgccag | 480 | |
| cagccgcggt aatacgtagg gtgcaagcgt tatccggaat tattgggcgt aaagggctcg | 540 | |
| taggcggttc gtcgcgtccg gtgtgaaagt ccatcgctta acggtggatc cgcgccgggt | 600 | |
| acgggcgggc ttgagtgcgg tagggagac tggaattccc ggtgtaacgg tggaatgtgt | 660 | |
| agatatcggg aagaacacca atggcgaagg caggtctctg ggccgttact gacgctgagg | 720 | |
| agcgaaagcg tggggagcga acaggattag ataccctggt agtccacgcc gtaaacggtg | 780 | |
| gatgctggat gtggggcccg ttccacgggt tccgtgtcgg agctaacgcg ttaagcatcc | 840 | |
| cgcctgggga gtacggccgc aaggctaaaa ctcaaagaaa ttgacggggg cccgcacaag | 900 | |
| cggcggagca tgcggattaa ttcgatgcaa cgcgaagaac cttacctggg cttgacatgt | 960 | |
| tcccgacggc cgtagagata cggcttccct tcggggcggg ttcacaggtg gtgcatggtc | 1020 | |
| gtcgtcagct cgtgtcgtga gatgttgggt taagtcccgc aacgagcgca accctcgccc | 1080 | |
| cgtgttgcca gcggattatg ccgggaactc acggggacc gccggggtta actcggagga | 1140 | |
| aggtggggat gacgtcagat catcatgccc cttacgtcca gggcttcacg catgctacaa | 1200 | |
| tggccggtac aacgggatgc gacgcggcga cgcggagcgg atccctgaaa accggtctca | 1260 | |
| gttcggatcg cagtctgcaa ctcgactgcg tgaaggcgga gtcgctagta atcgcgaatc | 1320 | |
| agcaacgtcg cggtgaatgc gttccccggcc cttgtacaca ccgcccgtca agtcatgaaa | 1380 | |
| gtgggcagca cccgaagccg gtggcctaac cccttgtggg atggagccgt ctaaggtgag | 1440 | |
| gctcgtgatt gggactaagt c | 1461 | |

PROBIOTIC FOR INFANTILE COLIC

The present invention relates to the fields of medicine, microbiology and nutrition and, particularly, to a novel probiotic composition based on *Pediococcus pentosaceus* cells. Due to their biofunctionalities, the composition is especially useful in the amelioration of excessive crying in infants.

BACKGROUND OF THE INVENTION

Excessive crying is one of the most frequent causes of visiting pediatricians in infant's first twelve months of life. Its incidence ratio can reach values up to 40%. Infants whom crying persist beyond three months are at risk of adverse outcomes in the school years including anxiety, aggression, hyperactivity, allergy, sleep disorders and even more risk of poor mental health in later years. Excessive crying is not only a serious problem for infants but also for parents and, in general, for family quality of life. Excessive crying leads to parental exhaustion and has many deleterious consequences including difficulties with concentration, loss of patience, frustration, feeling of incompetence, fear of harming the child, early cessation of breastfeeding and reduction of face-to-face interaction with their child. Furthermore, in some cases frustration may result in some kinds of deleterious actions to stop crying such as slapping or shaking the child.

Despite infant crying is commonly associated with evident illness conditions, excessive paroxysmal crying may manifest for no clear reason in apparently healthy and well-fed infants as a result of different conditions of unknown etiology (e.g. infant colic). There is little agreement regarding the origin of such conditions and how they should be defined. However, it has been proposed that they may be well caused by gastrointestinal disturbances, such as immaturity of the gut, spastic colon, food hypersensitivity, altered gut microbiota and gas production.

Traditionally, different drug therapies have being used for reduction of crying and fussing, especially in 'colicky infants'. One of the most common used drugs is simethicone, but results of clinical trials are not conclusive. Other treatments, based on dicyclomine hydrochloride or cimetropium bromide, have been shown to me more effective, but may lead to undesirable side effects, which limit their use, especially in infants less than 6 months of age.

Herbal remedies have been proposed as an alternative, although scientific evidence is scarce. The commercially available composition ColiMil® (with plant extracts from *Matricaria recutita*, *Foeniculum vulgare* and *Melissa officinalis*) was shown to reduce crying time in a double-blind placebo-controlled clinical trial. In contrast, *Mentha piperita* extracts has been reported to be ineffective for treatment of infant colic. Moreover, several adverse effects including vomiting, sleepiness, constipation and loss of appetite have been identified in several studies evaluating herbal supplements.

Infant formulas designed to overcome food allergies (i.e. formulas with low lactose content or partially hydrolyzed whey proteins) have been reported to reduce crying episodes. However, these formulas may benefit those infants whose excessive crying is associated mainly to food allergies. High fiber or fiber-enriched formulas have also been proposed as a possible treatment, but no significant differences in symptoms have been found when comparing with a standard formula.

Based on the hypothesis that aberrant intestinal microflora may contribute to excessive crying conditions, great interest on probiotics as a promising treatment has arisen. Probiotics are defined as "living microorganisms, which upon ingestion in certain amounts, exert health benefits beyond inherent basic nutrition". Several lactic acid bacteria and species from the genus *Bifidobacterium* or *Lactobacillus* are probiotic, which implies that they have been shown to promote specific health benefits. Probiotic bacteria must fulfill several requirements related to lack of toxicity, viability, adhesion and beneficial effects. These probiotic features are strain-dependent, even among bacteria of the same species. Therefore, it is important to find those strains exerting the desired probiotic functions.

Only few probiotic compositions for treatment of excessive crying have been studied. The efficacy of a probiotic formula comprising *Lactobacillus rhamnosus* GG, *Lactobacillus rhamnosus* LC705, *Bifidobacterium breve* Bbi99 and *Propionibacterium freudenreichii* ssp. *shermanii* JS has been studied without satisfactory results on crying patterns (Mentula, S. et al. "Microbial composition and fecal fermentation end products from colicky infants—A probiotic supplementation pilot", *Microbial Ecology in Health and Disease* 2008, vol. 20, no. 1, pp. 37-47). Another study evaluated the effect on colic of an alpha-lactalbumin-enriched and probiotic-supplemented formula (*Lactobacillus rhamnosus*, *Bifidobacterium infantis*). The formula reduced feeding-related gastrointestinal side effects, irritability and agitation, but no differences were found in crying duration (Dupont, C. et al. "A-Lactalbumin-Enriched and Probiotic-Supplemented Infant Formula in Infants with Colic: Growth and Gastrointestinal Tolerance" *European Journal of Clinical Nutrition* 2010, vol. 64, no. 7, pp. 765-767). The beneficial effects of *Lactobacillus reuteri* DSM 17938 for treatment of colic-related excessive crying have been disclosed in WO2007142596. The efficacy of this strain was assayed with favorable outcomes on infant crying (Savino, F. et al. "*Lactobacillus reuteri* (American Type Culture Collection Strain 55730) versus Simethicone in the Treatment of Infantile Colic: A Prospective Randomized Study" *Pediatrics* 2007, vol. 119, no. 1: e124-e130; Savino, F. et al. "*Lactobacillus reuteri* DSM 17938 in Infantile Colic: A Randomized, Double-Blind, Placebo-Controlled Trial" *Pediatrics* 2010, vol. 126, no. 3: e526-e533; Szajewska, H. et al. "*Lactobacillus reuteri* DSM 17938 for the Management of Infantile Colic in Breastfed Infants: A Randomized, Double-Blind, Placebo-Controlled Trial", *Journal of Pediatrics* 2012, vol. 162, no. 2, pp. 257-262), but was unable to improve intestinal biodiversity (Roos, S. et al. "454 Pyrosequencing Analysis on Faecal Samples from a Randomized DBPC Trial of Colicky Infants Treated with *Lactobacillus reuteri* DSM 17938", *PLoS ONE* 2013, vol. 8, no. 2, e56710 1-5).

In a recent article about the study of intestinal microbiota of infants with colic, it has been proposed that excessive crying may be caused by increased inflammation due to a higher level of pathogens and to a reduction in anti-inflammatory lactobacilli (De Weerth, C. et al. "Intestinal Microbiota of Infants With Colic: Development and Specific Signatures" *Pediatrics* 2013, vol. 131, Number 2, e550-e558).

WO2007142596 discloses that the strain of *Lactobacillus reuteri* DSM17938 is useful in the treatment of infant colic due to its ability to promote high amounts of the anti-inflammatory cytokine IL-10.

*Pediococcus pentosaceus* and *Pediococcus acidilactici* are commonly used in the fermentation of vegetables and meats and added in fodders as food preservatives to inhibit the growth of food-spoiling bacteria and foodborne pathogens. However, it is believed that there are not products in the market based on *Pediococcus pentosaceus* for use as probiotic in humans.

A plant derived *Pediococcus pentosaceus* strain has been disclosed as inducer of secretion levels of interferon-gamma and interleukin IL-12 p70, and suppressor IL-4 productions in ovalbumin sensitized mouse spleen cells. Therefore, the bacteria could effectively stimulate immune activities and showed allergic inhibitory effects due to the induction of such pro-inflammatory cytokines (Jonganurakkun, B. et al. "*Pediococcus pentosaceus* NB-17 for probiotic use", *Journal of Bioscience and Bioengineering* 2008 vol. 106, Issue 1, p. 69-73).

In the same direction, Igarashi T. 2010 discloses that the strain *Pediococcus pentosaceus* (KKM122) strongly induces the production of the pro-inflammatory cytokine IL-12 (Igarashi T. "Study of the relationship between changes in lactic acid bacterial cell components and stimulation of IL-12 production under salt-stressed conditions", *Bioscience, Biotechnology and Biochemistry* 2010, 74, pp. 2171-2175).

Vitali et al. 2012 discloses a study of forty-eight strains of lactic acid bacteria belonging to different species, for their capacity to modulate the synthesis of 27 immune-mediators (cytokines, chemokines and growth factors). Among such immune-mediators, the assay was prepared to detect IL-10. The assay was performed with Caco-2 and PBMC cells stimulated with LPS. The results indicated that few chemokines were stimulated. Immune-mediators with pro-inflammatory activity (IL-17, eotaxin and interferon-gamma) were significantly stimulated by all strains, followed by the cytokine IL-1 beta, the chemokine interferon-gamma-induced protein-10 (IP-10), the cytokine IL-6, and the chemokine macrophage inflammatory protein-1 alpha (MIP-1 alpha). Only few strains increased the synthesis of cytokines with anti-inflammatory activity. Among the strains tested, a strain of *Pediococcus pentosaceus* isolated from tomato stimulated cytokines IL-1 beta, IL-4, IL-17, and interferon-gamma, but not IL-10. Based on the immune-modulation activity this strain was not selected in the study for further characterization as novel probiotic candidate (Vitali, B. et al. "Novel probiotic candidates for humans isolated from raw fruits and vegetables", *Food Microbiology* 2012, 31(1), pp. 116-125).

Therefore, it is clear that excessive paroxysmal crying can have immediate and very serious consequences for both parents and infants. Thus, safe and effective compositions and treatments are required. In this field, probiotics can be considered as a promising alternative to current therapies, but further research is needed.

SUMMARY OF THE INVENTION

The problem to be solved by the present invention is to provide new compositions and remedies useful in the amelioration of excessive crying in infants.

The solution is based on new strains of *Pediococcus pentosaceus* that the present inventors have found which have relevant biofunctionalities useful in the amelioration of excessive crying in infants.

It is important to note first that the bacteria most commonly used in probiotic formulations are from *Lactobacillus* and *Bifidobacteria* genus. Thus, *Pediococcus* genus is very rare for using as probiotic and even more unusual for children.

As mentioned above the prior art has described that excessive crying may be caused by increased inflammation by an increased level of pathogens and by a reduction in anti-inflammatory lactobacilli. It has also been described that *Lactobacillus reuteri* DSM 17938 (derived from *L. reuteri* ATCC 55730) is useful in the treatment of infant colic by its ability to promote high amounts of the anti-inflammatory cytokine interleukin-10 (IL-10). Thus, it seems that the ability to increase the amounts of IL-10 is related to the amelioration of crying.

However, it is believed that the prior art has not described a *Pediococcus pentosaceus* strain with this feature. In fact, the relevant prior art describes *Pediococcus pentosaceus* strains having features which are completely in the opposite direction to the present invention. Thus, the ability of inducing the production of IL-10 is not an intrinsic or inherent feature of *Pediococcus pentosaceus* bacteria. For instance, Igarashi T. 2010 discloses a strain of *Pediococcus pentosaceus* (KKM122) which strongly induces the production of the pro-inflammatory cytokine IL-12, thus causing inflammation, which is the opposite effect than that of the present invention. Furthermore, Vitali et al. 2012 discloses a extensive study which enables the determination of 27 immune-mediators including IL-10. However, only few strains increased the synthesis of cytokines with anti-inflammatory activity and although a strain of *Pediococcus pentosaceus* isolated from tomato stimulated cytokines IL-1 beta, IL-4, IL-17, and interferon-gamma, it had no effect on IL-10. It is relevant to mention that the assay used in Vitali et al. 2012 to determine IL-10 is very similar than the described in the present invention, but remarkably, no strain of *Pediococcus pentosaceus* is identified in Vitali et al. 2012 having the ability of inducing IL-10.

In summary, when looking the prior art for bacteria that have this property, *Pediococcus pentosaceus* is not found among the bacterial species having this property. Thus, it is believed that no prior art describes a bacterial composition which comprises from $10^4$ to $10^{12}$ cfu/g of *Pediococcus pentosaceus* cells which have the ability to induce the production of IL-10 to reduce inflammation in the intestinal tract as described herein.

Surprisingly, the inventors have found a strain of *Pediococcus pentosaceus* that has the ability to induce the production of IL-10. Looking at the prior art, it could not be known that *Pediococcus pentosaceus* bacteria have these features.

Therefore, the strain *Pediococcus pentosaceus* CECT 8330 is provided herein. Furthermore, by means of the screening method described in detail, it is plausible to identify and isolate strains of *Pediococcus pentosaceus* other than strain CECT 8330 within a pool of *Pediococcus pentosaceus* cells, with the same ability to induce the production of IL-10.

Therefore, the present invention provides as one aspect, the strain of *Pediococcus pentosaceus* CECT 8330. The invention describes certain biological features in bacteria which are relevant for the amelioration of excessive crying; i.e. the ability to induce the production of IL-10 as the most relevant feature. Herein it is demonstrated by means of the Examples that said feature is plausibly related to the amelioration of excessive crying in infants. Thus, although one strain of *Pediococcus pentosaceus* with this feature has been identified (CECT 8330), without being limited to theory, there is no reason to limit the scope of the invention to such strain because all the steps of the method to get other good strains are plausibly described herein. Therefore, the invention also provides a pool of strains of *Pediococcus pentosa*-

*ceus* other than strain CECT 8330 that have the same feature. Not all the strains belonging to *Pediococcus pentosaceus* species will have the ability to induce IL-10. The invention provides a method to recognize them.

Accordingly, a first aspect of the invention relates to a bacterial composition which comprises from $10^4$ to $10^{12}$ cfu/g of *Pediococcus pentosaceus* cells which have the ability to induce the production of interleukin-10, wherein the production of interleukin-10 by THP-1 macrophages in the presence of *Pediococcus pentosaceus* cells expressed as normalized increase is higher than the production of the interleukin-10 by the negative control, which are THP-1 macrophages in the absence of *Pediococcus pentosaceus* cells, when the normalized increase is determined by the following steps:
  (a) differentiating THP-1 monocytes into macrophages by growing the THP-1 monocyte cell line obtained from the cell collection of the Public Health England, catalogue number 88081201, in Roswell Park Memorial Institute RPMI 1640 medium with 10% Fetal Bovine Serum FBS, and with phorbol 12-myristate 13-acetate (PMA) to a final concentration of 0.16 µM;
  (b) growing the THP-1 macrophages in RPMI 1640 medium with 10% FBS in 24-wells ELISA plates to a final concentration of $10^6$ macrophages/well;
  (c) incubating for 2.5 hours the THP-1 macrophages with lipopolysaccharide (LPS) at a final concentration of 10 ng/ml, and washing the THP-1 macrophages with Dulbecco's Phosphate Buffered Saline medium D-PBS;
  (d) getting a culture of *Pediococcus pentosaceus* cells ready by having grown it overnight in Man, Rogosa and Sharpe medium (MRS) at 37° C. in a 5% $CO_2$ atmosphere;
  (e) adding to each ELISA-well 500 µl of RPMI 1640 medium with 10% FBS and an appropriate amount of a dilution of *Pediococcus pentosaceus* cells to obtain a final ratio of 25:1, i.e. $2.5 \times 10^7$ cfu of *Pediococcus pentosaceus* cells:$10^6$ THP-1 macrophages;
  (f) incubating the THP-1 macrophages with the *Pediococcus pentosaceus* cells for 2.5 hours at 37° C. or without the *Pediococcus pentosaceus* cells in the same conditions as negative control;
  (g) washing the THP-1 macrophages with D-PBS medium to remove the *Pediococcus pentosaceus* cells, subsequently adding to the THP-1 macrophages RPMI 1640 medium with 10% FBS supplemented with 50 µg/ml gentamicin, 10 µg/ml ampicillin and 12 µg/ml chloramphenicol, incubating at 37° C. at 5-7% $CO_2$, and taking aliquots at 5 and 24 hours;
  (h) centrifuging the aliquots and assaying the supernatants for interleukin-10 quantification by flow cytometry; and
  (i) calculating the normalized increase of interleukin-10 concentration, with the formula $(IL10_{24\,h} - IL10_{5\,h})/IL10_{5\,h}$, wherein $IL10_{5\,h}$ and $IL10_{24\,h}$ is the concentration of interleukin-10 in pg/ml at 5 or 24 hours, respectively.

Thus, based on the detailed assay described herein (see EXAMPLE 1 for the IL-10 induction assay) the skilled person is routinely able to repeat this assay to objectively determine whether *Pediococcus pentosaceus* of interest complies with the IL-10 levels of the first aspect of the invention. Within the *Pediococcus pentosaceus* cells that comply with IL-10 induction levels, the deposited strain *Pediococcus pentosaceus* CECT 8330 is herein provided.

The novel bacterial composition as described herein is useful as a probiotic supplement for humans and particularly for infants. Accordingly, a second aspect of the invention relates to the bacterial composition as defined herein for use in the amelioration of excessive crying in infants. In this sense it is believed that no prior art has described *Pediococcus pentosaceus* cells for using in the amelioration of excessive crying in infants.

This aspect can be alternatively formulated as the use of a bacterial composition as defined in the first aspect of the invention for the manufacture of a food supplement, a medicament, an infant formula, an edible product or a food product for the amelioration of excessive crying in infants. This may be alternatively formulated as a method for ameliorating excessive crying in infants, comprising administering to said infant an effective amount of the bacterial composition as defined in the first aspect of the invention.

Another aspect of the invention is the bacterial composition as defined gerein for use as a medicament.

The term "effective amount" as used herein is the amount of colony forming units (cfu) for each strain in the composition that is high enough to significantly modify the condition to be treated in a positive way but low enough to avoid serious side effects (at a reasonable benefit/risk ratio), within the scope of sound medical judgment.

A third aspect of the invention relates to the strain of *Bifidobacterium longum* CECT 7894.

Finally, a fourth aspect of the invention relates to a method for screening and isolating novel *Pediococcus pentosaceus* cells comprising the following steps:
  (i) assaying new *Pediococcus pentosaceus* cells from a pool of *Pediococcus pentosaceus* cells for their ability to induce the production of IL-10 by following the steps of the IL-10 induction assay described above; and
  (ii) selecting and isolating the new *Pediococcus pentosaceus* cells from the pool that induces a production of IL-10 expressed as normalized increase higher than the normalized increase of the negative control, when the normalized increase is determined following the steps of the IL-10 induction assay.

It is evident to the skilled person that once the inventors herein have disclosed the relevant test assay plus the deposited strain CECT 8330 that complies with the IL-10 levels of induction, it will be routine work for the skilled person to select other new *Pediococcus pentosaceus* cells complying with the criteria of the first aspect of the invention.

DETAILED DESCRIPTION OF THE INVENTION

The term "bacterial composition" shall be understood according to the art as a composition comprising a number of bacteria cells wherein from $10^4$ to $10^{12}$ cfu/g are from *Pediococcus pentosaceus* cells with the characteristic of interest according to the first aspect. The bacterial composition can contain additives such as carriers or excipients. The bacterial composition is then packed into a suitable container.

The term "cfu/g" relates to the gram weight of the composition as such, including relevant additives present in the composition. It does not include the weight of a suitable container used to package the bacterial composition.

The first aspect of the invention relates to a bacterial composition which comprises from $10^4$ to $10^{12}$ cfu/g of *Pediococcus pentosaceus* cells which have the ability to induce a production of interleukin-10 by THP-1 macrophage cells higher than the production of IL-10 by THP-1 macrophage cells in the absence of *Pediococcus pentosaceus* cells, when the normalized increase is determined by the steps mentioned above.

IL-10, also known as human cytokine synthesis inhibitory factor (CSIF), is an anti-inflammatory cytokine that inhibits the synthesis of a number of cytokines, including IFN-gamma, IL-2, IL-3, TNF, and GM-CSF produced by activated macrophages and by helper T cells. The term cytokine refers to a small signaling molecule used for cell signaling. Cytokines can be classified as proteins, peptides or glycoproteins. In this case, IL-10 is a protein cytokine with immunomodulatory properties.

In a particular embodiment, the production of IL-10 by THP-1 cells in the presence of *Pediococcus pentosaceus* cells expressed as normalized increase is at least 2-fold higher than the production of IL-10 by THP-1 cells in the absence of *Pediococcus pentosaceus* cells, when the normalized increase is determined by the steps mentioned above. In other particular embodiments, the normalized increase is at least 3-fold, 4-fold, 5-fold or 6-fold higher than the control.

Further to the ability to induce the production of IL-10, the *Pediococcus pentosaceus* cells have interesting antagonism properties against undesirable members of bacterial species commonly abundant in infants with excessive crying (see EXAMPLE 2). The term "antagonism" is understood herein as inhibition or reduction of bacterial growth. Accordingly, in another particular embodiment, the *Pediococcus pentosaceus* cells of the bacterial composition have the ability to antagonize Gram positive and Gram negative intestinal bacteria. Particularly, the Gram positive bacteria comprise bacteria selected from the group consisting of *Clostridium difficile* and *Enterococcus faecalis*. In another particular embodiment, Gram negative bacteria comprise bacteria selected from the group consisting of *Escherichia coli, Enterobacter aerogenes, Klebsiella oxytoca* and *Bacteroides vulgatus*. In another particular embodiment, the *Pediococcus pentosaceus* cells have the ability to antagonize *Clostridium difficile, Enterococcus faecalis, Escherichia coli, Enterobacter aerogenes, Klebsiella oxytoca* and *Bacteroides vulgatus*, wherein the ability to antagonize is determined by the following steps:
(i) swabbing uniformly pathogen strains in plates containing Oxoid medium and growing to confluence in a $CO_2$ incubator at the appropriate temperatures and % $CO_2$ for the growth of each pathogen;
(ii) placing two 6 mm diameter cylinder sections of a uniformly seeded confluent agar plate of the *Pediococcus pentosaceus* cells in contact with the pathogen seeded plate, confronting both (a) the grown side of one cylinder section against the pathogen seeded plate; and (b) the non-grown side of the other cylinder section against the pathogen seeded plate; and incubating overnight at 37° C.;
(iii) measuring next day the inhibition zones by placing the agar plate over a flat rule; and
(iv) calculating the growth inhibitory activity by subtracting the cylinder diameter (CD) from the inhibition zone diameter (IZD) measured in centimeters and dividing this difference by 2, following the formula GI=(IZD-CD)/2.

In a particular embodiment, the *Pediococcus pentosaceus* cells are from *Pediococcus pentosaceus* deposited in the Spanish Type Culture Collection under the accession number CECT 8330.

*Pediococcus pentosaceus* CECT 8330

A sample of the novel *Pediococcus pentosaceus* strain has been deposited at CECT (Colección Española de Cultivos Tipo) in the Edificio 3 CUE, Parc Cientific Universitat de València, Catedrático Agustin Escardino, 9, 46980 Paterna, Valencia (Spain) by the depositor AB-Biotics S.A., sited at Edifici Eureka, office P1M1.1, Campus UAB, 08193-Bellaterra (Spain). The strain was deposited under the accession number CECT 8330 with a deposit date of Apr. 30, 2013. The deposit was made under the conditions of the Budapest Treaty on the International Recognition of the Deposit of Microorganisms for the Purposes of Patent Procedure. The identification reference given by the depositor was F3403.

As shown in the examples below, *Pediococcus pentosaceus* CECT 8330 displays the following interesting properties for the amelioration of excessive crying in infants:
Ability to induce IL-10 production as shown in TABLE 1, EXAMPLE 1.
Inhibitory activity against all the spectrum of pathogens studied (TABLE 2, EXAMPLE 2). The strain is effective inhibiting not only Gram positive but also Gram negative bacteria. This is of great interest as it provides protection against bacteria such as *E. coli, Klebsiella* and *Clostridium* spp. which are abnormally abundant in infants presenting excessive crying.
No production of ethanol and $CO_2$, thus not causing disturbances to infants.

Furthermore, the strain CECT 8330 has the advantage of being particularly useful as a probiotic. Probiotic bacteria must fulfill several requirements related to lack of toxicity, viability, adhesion and beneficial effects. The properties of each bacterial strain are unique and cannot be extrapolated to other strains of the same species. Therefore, it is important to find those strains that have a better performance in all probiotic requirements. To ensure that strain CECT 8330 was able to overcome the gastrointestinal (GI) tract, an in vitro protocol was developed mimicking its conditions. Survival after treatment with lysozyme, hydrogen peroxide, acidic environment and bile salts was quantified. This is a confirmatory experiment since strains were isolated from human feces using very high dilutions and their presence in feces is high. The results indicate that the strain is capable to survive the passage of the GI tract.

Strain CECT 8330 was also assayed for its ability to colonize the intestinal tract. This is a critical point since it ensures that the observed biofunctionalities can be developed by the strain. In the experimental development intestinal mucus and Caco-2 cells were used, which mimics the colon anchorage sites of the probiotic strains. Adhesion capacity of the strain was measured from scintillation of tritium-labeled thymidine and compared to those of *Lactobacillus reuteri* strain used as a control. Mucus cells adhesion and Caco-2 cells adhesion was $1.40 \times 10^6$ and $4.5 \times 10^6$ cfu/cm$^2$ respectively (*L. reuteri*: $6.58 \times 10^6$ and $1.01 \times 10^6$ cfu/cm$^2$). Thus, the results indicate that CECT 8330 have good adhesion to the intestinal epithelium, comparable to *L. reuteri*, which allows it to remain in the intestinal tract and to exert their probiotic effects.

The strain CECT 8330 has a good growth in industrial medium.

Further, strain CECT 8330 belongs to a bacterial species that has QPS status (Andreoletti, O. et al. "The maintenance of the list of QPS microorganisms intentionally added to food or feed. Question no: EFSA-Q-2008-006", *The EFSA Journal* 2008. 923: p. 1-48). QPS ("Qualified Presumption of Safety") is a system developed by the European Food Safety Authority to grant status to taxonomical units with a proven long history of apparent safe use.

*Bifidobacterium longum* CECT 7894

In another particular embodiment, the bacterial composition further comprises from $10^4$ to $10^{12}$ cfu/g of cells of *Bifidobacterium longum* CECT 7894.

A sample of the novel *Bifidobacterium longum* strain has been deposited at CECT (Colección Española de Cultivos Tipo) in the Edificio 3 CUE, Parc Cientific Universitat de València, Catedrático Agustin Escardino, 9, 46980 Paterna, Valencia (Spain) by the depositor AB-Biotics S.A., sited at Edifici Eureka, office P1M1.1, Campus UAB, 08193-Bellaterra (Spain). The strain was deposited under the accession number CECT 7894 with a deposit date of Mar. 30, 2011. The deposit was made under the conditions of the Budapest Treaty on the International Recognition of the Deposit of Microorganisms for the Purposes of Patent Procedure. The identification reference given by the depositor was Bif F2.

The strain *Bifidobacterium longum* CECT 7894 has also interesting properties for the amelioration of excessive crying in infants as shown in the Examples:

Ability to induce IL-10 production as shown in TABLE 1, EXAMPLE 1.

Inhibitory activity against all the spectrum of pathogens studied (TABLE 2, EXAMPLE 2). The strain is effective inhibiting not only Gram positive but also Gram negative bacteria. See comments for strain CECT 8330.

No production of ethanol and $CO_2$, thus not causing disturbances to infants.

As for *Pediococcus pentosaceus* strain CECT 8330, *Bifidobacterium longum* CECT 7894 was also assayed for its ability to overcome the gastrointestinal (GI) tract. The results indicated that the strain is capable to survive the passage of the GI tract.

The strain CECT 7894 was also assayed for its ability to colonize the intestinal tract, following the assay above mentioned for *Pediococcus pentosaceus*. Mucus cells adhesion and Caco-2 cells adhesion for strain CECT 7894 was $1.21 \times 10^5$ and $1.18 \times 10^6$ cfu/cm$^2$, respectively (*L. reuteri*: $6.58 \times 10^6$ and $1.01 \times 10^6$ cfu/cm$^2$). Thus, the results indicate that CECT 7894 have good adhesion to the intestinal epithelium, comparable to *L. reuteri*, which allows it to remain in the intestinal tract and to exert their probiotic effects.

The strain CECT 7894 has also a good growth in industrial medium.

Therefore, both strains, *Pediococcus pentosaceus* CECT 8330 and *Bifidobacterium longum* CECT 7894 share various functional properties that make them suitable for their use in the amelioration of excessive crying in infants, by using the strains separately or together in a single formula. Among other properties, they both have the ability to induce IL-10 production, and they are efficient inhibiting the growth of intestinal bacteria (Gram positive but also Gram negative bacteria).

Furthermore, the strains have the advantage that they do not produce gas. Heterofermentative bacteria produce $CO_2$ and ethanol, as well as lactic acid, by glucose fermentation. Ethanol could influence intestinal motility producing abdominal distension characteristic of colicky infants. $CO_2$ can lead to meteorism (accumulation of gas) and flatulence, also typical of colicky infants. It has been described a higher presence of heterofermentative strains in colicky infants. In contrast, the strains of the invention do not produce ethanol nor $CO_2$, thus not causing disturbances to infants in this sense.

As will be apparent to the skilled in the art, *Pediococcus pentosaceus* CECT 8330 and *Bifidobacterium longum* CECT 7894 are effective when used on their own or when combined in a single composition. They can also be administered in two different compositions administered simultaneously, sequentially or separately after a certain period of time.

Given the properties described above, the bacterial composition exerts a physiological improvement in the aforementioned causes of crying that leads to an amelioration of some of the clinical symptoms related to excessive crying. Accordingly, the bacterial composition of the invention is especially useful in the amelioration of excessive crying in infants. The term "excessive crying" is understood herein as intense, persistent and inconsolable crying, problematic for the normal family unit functioning, which implies at least 60 minutes per day (in 3 or more episodes) observed during at least 1 week.

The term "infant" shall be understood in this description as the very young offspring of a human or animal. When applied to humans, the term is considered synonymous with the term "baby". The term "child" refers to a human between the stages of birth and puberty. "Child" also describes a relationship with a parent, as a synonym of "son" and "daughter". However, in this description, the terms "infant", "baby" and "child" are considered synonymous and are used interchangeably.

In a particular embodiment, the bacterial composition of the invention is useful in the amelioration of excessive crying associated to infant colic. The term "infant colic" is understood herein as unexplained and inconsolable crying ("fussy") which causes distress to parents. The term "fussy" is a very subjective measure due to the difficulty for parents and physicians to categorize the type of crying. Besides, excessive crying behavior (easy to calm or not) may be indicative of colic. Consequently, one of the most often cited inclusion criteria of colicky infants is based on a time rule (i.e. based on Wessel's criteria) as: more than 3 hours of crying per day for at least 1 week (Savino, F. et al. 2010 supra).

In another embodiment of the invention, infants have an age from three weeks to twelve months.

A pilot clinical trial with 20 infants was conducted to evaluate the efficacy and safety a product based on a mixture of the strains CECT 8330 and CECT 7894 (see EXAMPLE 7). Placebo and the mixture of strains were administered once per day (5 drops/day) for 14 days. As it can be seen in FIG. 3, the probiotic formula caused a greater reduction in the average daily crying time and in the duration of each episode. No adverse effects were observed in either placebo or probiotic group, confirming that the probiotic formula can be considered safe. Hence, the mixture of strains is useful for ameliorating crying patterns.

From the relevant properties of the bacterial composition explained above, it is derived that the administration of the bacterial composition, it is also useful to treat other conditions characterized by gastrointestinal disturbances associated to inflammation as consequence of the immaturation of the immune system; to treat intestinal hypersensitivity and to balance excess of undesirable bacteria in the intestine.

Considering the properties mentioned above, the strains CECT 8330 and 7894 have a better performance for the parameters studied which are relevant for excessive crying when compared with commercial strains known in the art. As shown in the examples below, strain CECT 8330 showed a better normalized increase related to the induction of IL-10 production, compared to the one of the *Lactobacillus reuteri* strain. Furthermore, the strains of the invention displayed inhibitory activity against all the spectrum of pathogens studied. The strains of the invention were effective inhibiting not only Gram positive but also Gram negative bacteria.

This was not the case of *L. reuteri* which was inefficient inhibiting the growth of *E. coli* and *B. vulgatus*. This is of great interest as abnormal amounts of bacteria such as *E. coli* are commonly present in infants presenting excessive crying. It is also noteworthy that, in general, CECT 8330 and specially CECT 7894, were more efficient inhibiting the growth of almost all the pathogen bacteria compared to *L. reuteri*. Moreover, the strains CECT 8330 and CECT 7894 did not produced gas while *L. reuteri* did produce gas.

Assay to Measure the Induction of IL-10 Production

Working EXAMPLE 1 herein provides a detailed description of an assay suitable to measure the induction of IL-10 production, as it is referred to steps (a)-(i) of the first aspect of the present invention. It is relevant to note that the descriptions and conditions of the IL-10 induction assay disclosed in steps (a)-(i) of the first aspect and in EXAMPLE 1 are not limiting the scope of the invention. The assay is one suitable to test the ability of *Pediococcus pentosaceus* cells to induce IL-10 production. The detailed conditions of this EXAMPLE 1 form herein a preferred assay to determine if *Pediococcus pentosaceus* cells of interest comply with the criteria of the first aspect.

Accordingly, based on the detailed assay described herein the skilled person is routinely able to repeat this assay to objectively determine whether *Pediococcus pentosaceus* cells of interest comply with the induction in IL-10 production of the first aspect.

When the described assay is used, according to the first aspect the levels of IL-10 produced by THP-1 cells in the presence of *Pediococcus pentosaceus* cells expressed as normalized increase are higher than the control. The control as it is understood herein and according to the first aspect is the normalized increase of the IL-10 produced by THP-1 cells in the absence of *Pediococcus pentosaceus* cells. In a particular embodiment the levels of IL-10 produced by THP-1 cells in the presence of *Pediococcus pentosaceus* are at least 2-fold the level of the control. In other particular embodiments, the normalized increase is at least 3-fold, 4-fold, 5-fold or 6-fold higher than the control.

Assay to Measure Antagonism Capacity Against Intestinal Bacteria

Working EXAMPLE 2 herein provides a detailed description of an assay suitable to measure the capacity of *Pediococcus pentosaceus* cells to antagonize intestinal bacteria, as it referred in one embodiment of the invention. It is relevant to note that the descriptions and conditions of the assay disclosed in EXAMPLE 2 are not limiting the scope of the invention. The assay is one suitable to test the ability of *Pediococcus pentosaceus* cells to antagonize intestinal bacteria.

Accordingly, based on the detailed assay description herein the skilled person is routinely able to repeat this assay to objectively determine whether *Pediococcus pentosaceus* cells of interest comply with the bacterial spectrum detailed above; i.e. are able to antagonize *Clostridium difficile, Enterococcus faecalis, Escherichia coli, Enterobacter aerogenes, Klebsiella oxytoca* and *Bacteroides vulgatus*.

Compositions and Administration Forms

In a particular embodiment of the invention, the bacterial composition as defined above is in a form selected from the group consisting of a food supplement, a medicament, an infant formula, an edible product and a food product.

The bacterial composition of the invention may be prepared in any suitable form which does not negatively affect to the viability of the bacterial cells forming the composition of the invention. Selection of the excipients and the most appropriate methods for formulation in view of the particular purpose of the composition is within the scope of ordinary persons skilled in the art of pharmaceutical and food technology.

The bacterial composition according to the invention can be formulated in a form in which the bacterial cells are the only active agent or are mixed with one or more other active agents and/or are mixed with pharmaceutically acceptable excipients or adequate additives or ingredients in the case of a food product. In a particular embodiment of the invention, the composition additionally contains one or more further active agents. Preferably, the additional active agent or agents are other probiotic bacteria which are not antagonistic to the bacterial cells forming the composition of the invention. Depending on the formulation, the bacterial cells may be added as purified bacteria, as a bacterial culture, as part of a bacterial culture, as a bacterial culture which has been post-treated, and alone or together with suitable carriers or ingredients. Prebiotics can also be added.

The bacterial composition can be in the form of a pharmaceutical product. The term "pharmaceutical product" is understood in its widely meaning in this description, including any composition that comprises an active ingredient—in this case, the bacterial cells-together with pharmaceutically acceptable excipients. The term "pharmaceutical product" is not limited to refer to medicaments. The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The pharmaceutical product can adopt different forms or names depending on the product approval route and also depending on the country. For instance, a medicament is a particular pharmaceutical product. A medical food is considered in this description as another particular pharmaceutical product. The terms "medical food" or "food for special medical purposes" are used in some countries to refer to a food specially formulated and intended for the dietary management of a disease that has distinctive nutritional needs that cannot be met by normal diet alone. They are defined in regulations such as the Food and Drug Administration's 1988 Orphan Drug Act Amendments in the United States, and the Commission Directive 1999/21/EC in Europe. Medical foods are distinct from the broader category of food supplements and from traditional foods that bear a health claim. Thus, in a particular embodiment, the composition of the invention is a medical food.

Often, probiotic bacterial compositions such as the one disclosed herein, are considered as food supplements. A food supplement, also known as dietary supplement or nutritional supplement is considered another particular pharmaceutical product. This is a preparation intended to supplement the diet and provide nutrients or beneficial ingredients that are not usually ingested in the normal diet or may not be consumed in sufficient quantities. Mostly, food supplements are considered as food products, but sometimes they are defined as drugs, natural health products, or nutraceutical products. In the sense of the present invention, food supplements also include nutraceuticals. Food supplements are usually sold "over the counter", i.e. without prescription. If the food supplement adopts the form of a pill or a capsule, it comprises excipients which are the same as the used in medicaments. A food supplement however can also adopt the form of a food product which is fortified with some nutrients (e.g. an infant formula).

Thus, in a particular embodiment, the composition of the invention is a food supplement and more particularly an infant food supplement.

The composition according to the invention can be administered as such or mixed with a suitable edible liquid or solid, freeze-dried in the form of tablets, pills, capsules, lozenges, granules, powders, suspensions, sachets, syrups or usually in the form of a unit dose. It can also be in form of monodoses of freeze-dried composition presented together with a separate liquid container to be mixed before administration.

In the context of infants of very young age, the administration is limited to a few of administration forms. Thus, in a preferred embodiment, the bacterial composition of the invention is in the form of an oily suspension to be administered alone or mixed with a liquid. The oily suspension comprises at least one edible oil such as olive oil, maize oil, soybean oil, linseed oil, sunflower oil or rice oil. The oil is present in a quantity of at least 70% weight/weight. In a particular embodiment, the oily suspension also comprises at least one excipient which is an emulsifier, stabilizer or anti-caking agent, in an amount of 0.1-15% w/w. Suitable agents are silicon dioxide, silica gel, colloidal silica, precipitated silica, talc, magnesium silicate, lecithin, pectin, starch, modified starches, konjac gum, xanthan gum, gellan gum, carrageenan, sodium alginate, mono- or diglycerides of fatty acids such as glycerol monostearate or glycerol monooleate and citric acid esters of mono- or diglycerides.

The oily suspension is prepared according to techniques well known to those skilled in the art and using known machinery. A given quantity of oil is introduced into a container provided with stirring and heating means. Subsequently the at least one excipient is added under stirring and if necessary with slight heating to a temperature comprised from 20 to 50° C. to avoid the formation of lumps and agglomerations until complete homogenization. The suspension is cooled until room temperature and the bacterial cells in solid form are gradually added under stirring until complete homogenization of the suspension.

Particularly, the bacterial composition of the invention is in form of an infant food supplement in the form of oily suspension. In a particular embodiment the oily suspension comprises sunflower oil and colloidal silica, preferably at 1% by weight, and the bacterial cells.

In another embodiment the oily suspension comprises sunflower oil and an agent selected from lecithin, mono- or diglycerides of fatty acids, carrageenan and sodium alginate, and the bacterial cells.

The bacterial composition of the invention can also be included in a variety of food products or edible products, such as milk products in case of infants. The term "edible product" is used herein in its broadest meaning, including any type of product, in any form of presentation, which can be ingested by an animal; i.e. a product that is organoleptically acceptable. The term "food product" is understood as an edible product which also provides a nutritional support for the body. Particularly interesting food products are food supplements and infant formulas. The food product preferably comprises a carrier material such as oat meal gruel, lactic acid fermented foods, resistant starch, dietary fibers, carbohydrates, proteins and glycosylated proteins. In a particular embodiment, the bacterial cells of the invention are homogenized with other ingredients, such as cereals or powdered milk to constitute an infant formula.

Thus, it has to be understood that the bacterial composition of the invention is useful in the management of excessive crying in infants regardless of the form of the composition; i.e. regardless of being a pharmaceutical product, a medicament, a food product, an edible product, a food supplement, or a medical food.

Bacterial Cells Growth, Mutants and Doses

Bacteria are grown by cultivating them in a suitable medium and under suitable conditions. The bacterial cells of the invention can be cultivated alone to form a pure culture, or as a mixed culture together with other microorganisms, or by cultivating bacteria of different types separately and then combining them in the desired proportions. After cultivation, the cell suspension is recovered and used as such or treated in the desired manner, for instance, by concentrating, dehydrating, sprayed- or freeze-drying, to be further employed in the preparation of pharmaceutical or food products. Sometimes the probiotic preparation is subjected to an immobilization or encapsulation process in order to improve the shelf life. Several techniques for immobilization or encapsulation of bacteria are known in the art.

Another aspect of the invention relates to the herein described novel strain or "a mutant thereof". It is clear that by using the deposited strain as starting material, the skilled person in the art can routinely, by conventional mutagenesis or re-isolation techniques, obtain further mutants or derivatives thereof that at least retain the herein described relevant features and advantages of the strain forming the composition of the invention. Accordingly, the term "a mutant thereof" relates to mutant strains obtained by using the deposited strain as starting material. In one embodiment, the mutant is obtained by using recombinant DNA technology. In another embodiment of the first aspect of the invention, the mutant obtained by random mutagenesis. In a particular embodiment of the first aspect of the invention, the variant is a naturally occurring variant. This may alternatively be formulated as a method to obtain a strain, comprising using one of the herein deposited strains as starting strain, making mutants of the deposited strain and isolating a novel strain wherein the mutant has retained the essential properties of the deposited strain.

The effective amount of the bacterial cells will be determined by the skilled in the art and will vary with the particular goal to be achieved, the age and physical condition of the patient being treated, the severity of the underlying disorder, and the final formulation. When administered orally, the strains of the invention are present in the composition in an amount giving an effective daily dose of from $10^7$ to $10^{12}$ cfu, according to the current legislation, preferably from $10^9$ to $10^{11}$ cfu. The expression "colony forming unit" ("cfu") is defined as number of bacterial cells as revealed by microbiological counts on agar plates. When used in the form of the composition of the invention, the different strains are, preferably, in a concentration ratio of 1:1.

The general use of strains of the invention is in the form of viable cells. However, it can also be extended to non-viable cells such as killed cultures or cell lysates (obtained by e.g. exposure to altered pH, sonication, radiation, temperature or pressure, among other means of killing or lysing bacteria) or compositions containing beneficial factors produced by strains of the invention.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention.

EXAMPLES

Figure 1:
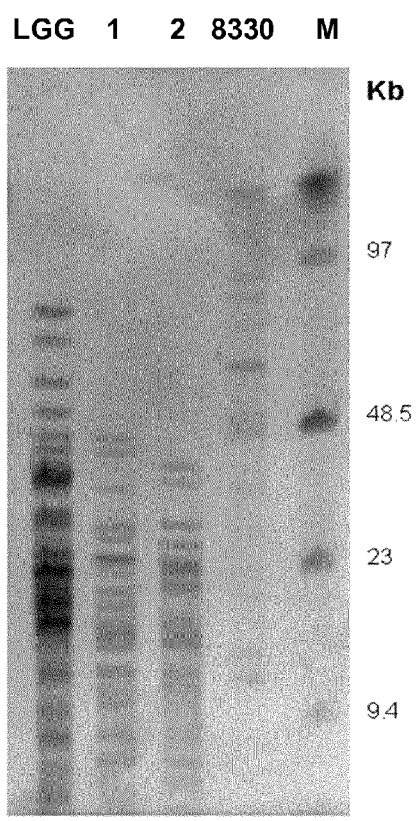
FIG. 1. Pulsed-field gel electrophoresis patterns of Sma-I (left) and Not-I (right) restricted genomic DNA of, from left to right: *Lactobacillus rhamnosus* GG (LGG), *Pediococcus pentosaceus* CECT 8330 (8330), two strains of *Pediococcus acidilactici* as controls (1, 2) and molecular marker (M).
Figure 1:
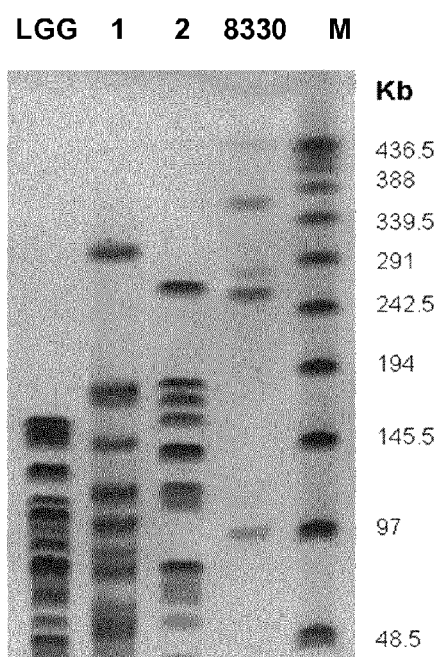

The strain *Lactobacillus reuteri* ATCC 55730 is used as a control in some experiments.

Example 1. In Vitro Evaluation of the Ability to Induce IL-10 Production in an Intestinal Mucosa Model The immunomodulatory capacity of the bacterial strains resulting from its interaction with the digestive tract's immune system (often referred to as gut-associated lymphoid tissue, GALT) was studied. More specifically, it was sought to test whether the bacterial strains have the ability to induce the production of anti-inflammatory IL-10 to reduce the inflammatory intestinal tract. The molecular basis for this is the interaction of probiotics cell surface receptors with TLR-2 and TLR-4 (Toll like receptor) that can be found on dendritic cells present in the Peyer's plates.

THP-1 Cell Line

The selected model was the cell line THP-1, which expresses TLR-2 and TLR-4. This model is sensitive to bacterial components like lipopolysaccharide—LPS—(as inducer of the inflammatory response), and is susceptible to modulate cytokine production when there are molecules in the medium suitable for the induction of the production of an anti-inflammatory cytokine pattern.

The term "THP-1 cell line" according to the art relates to a human monocytic cell line derived from an acute monocytic leukemia patient. It is used to test leukemia cell lines in immunocytochemical analysis of protein-protein interaction, and immunohistochemistry.

THP-1 cell line was obtained from the cell collection of the Public Health England (catalogue number 88081201). At the filing date of the present application the product catalogue for 88081201 from the provider Public Health England (www.hpacultures.org.uk) reads in relation to the THP-1 cells: "Human monocytic leukaemia. Derived from the peripheral blood of a 1 year old male with acute monocytic leukaemia".

Mediums and LPS

THP-1 monocytes were grown in Roswell Park Memorial Institute (RPMI) 1640 medium+10% Fetal Bovine Serum (FBS). RPMI was a standard commercially available medium (RPMI 1640, ref. 61870-010 from Gibco). FBS was also from Gibco.

THP-1 monocytes were differentiated into macrophages by adding to the grow medium 5 mg of phorbol 12-myristate 13-acetate (PMA, ref. P8139 from SIGMA) to a final concentration of 0.16 µM and incubating for approximately 72 hours.

The bacterial strains were grown in MRS medium. It was a standard commercial available Man, Rogosa and Sharpe medium (MRS, Broth Oxoid ref. CM0359).

THP-1 macrophages were stimulated with LPS to induce an inflammatory response. Lipopolysaccharides (LPS), also known as lipoglycans, are large molecules consisting of a lipid and a polysaccharide joined by a covalent bond; they are found in the outer membrane of Gram-negative bacteria, act as endotoxins and elicit strong immune responses in animals. LPS used in this study was a standard commercial available lipopolysaccharide (ref. L4391 from Sigma).

Grow, Incubations and IL-10 Measurement

THP-1 macrophages were grown in RPMI 1640+10% FBS medium in 24-wells ELISA plates to a final concentration of $10^6$ macrophages/well. Final cell concentration was calculated by using Tripan blue dye and a Neubauer-counting chamber.

THP-1 macrophages were co-incubated with LPS (final concentration 10 ng/ml) for 2.5 hours. Then cells were washed with Dulbecco's Phosphate Buffered Saline medium (D-PBS, ref. 14190-094 from Gibco). Five hundred µl of RPMI 1640+10% FBS medium were added to each ELISA-well.

The bacterial strains were previously grown overnight in MRS medium at 37° C. in a 5% $CO_2$ atmosphere. Bacterial strains appropriately diluted to obtain a final ratio of 25:1 ($2.5 \times 10^7$ cfu of bacteria:$10^6$ THP-1 macrophages) were added to each well. Concentration was calculated using a Neubauer-counting chamber.

THP-1 macrophages were then incubated for 2.5 hours at 37° C. with or without (negative control) bacterial strains. Subsequently, macrophages were washed twice with D-PBS medium to remove the bacterial strains. Then, RPMI 1640+10% FBS medium supplemented with gentamicin (50 µg/ml), ampicillin (10 µg/ml) and chloramphenicol (12 µg/ml) was added, incubated at 37° C. at 5-7% $CO_2$, and aliquots were taken at 5 and 24 hours.

Aliquots were centrifuged and the supernatants assayed for IL-10 by flow cytometry by using the commercial kit Human IL-10 Flex Set (Bead B7 ref. number 558274 from BD Biosciencies) following manufacturer instructions.

Calculations

For interpretation of results, absolute values were not used. The most informative value is the evolution of cytokines, in this case IL-10 concentration, expressed as normalized increase taking the values at 5 and 24 h. This reflects what happens in gut and provides a standard value allowing a transversal comparison between experiments. The normalized increase is calculated following the formula, wherein $IL10_{5\,h}$ and $IL10_{24\,h}$ is the concentration of IL-10 in pg/ml at 5 or 24 hours, respectively:

$$(IL10_{24\,h} - IL10_{5\,h})/IL10_{5\,h}$$

Results

The higher the value, the higher the induction of IL-10. As shown in TABLE 1, LPS-induced THP-1 macrophages induced the production of IL-10 in the presence of bacterial strains, IL-10 induction being especially high in the presence of the strain CECT 8330. The induction caused by CECT 8330 is slightly higher than the caused by *L. reuteri*.

TABLE 1

Normalized increases of IL-10 in LPS-induced THP-1 macrophages. "Negative control" corresponds to THP-1 macrophages incubated without bacterial strains

|  | IL-10$_{5\,h}$ in pg/ml | IL-10$_{24\,h}$ in pg/ml | Normalized increase |
|---|---|---|---|
| CECT 8330 | 30.83 | 140.18 | 3.54 |
| CECT 7894 | 23.87 | 57.43 | 1.40 |
| L. reuteri | 30.31 | 122.17 | 3.03 |
| Negative control | 27.56 | 43.24 | 0.56 |

Example 2. Antagonism Capacity Against Intestinal Bacteria

The objective was to assess the ability of bacterial strains to antagonize undesirable members of species commonly abundant in infants with excessive crying.

The protocol used for detecting and evaluating these capabilities is known as Campbell protocol. This technique involves incubating the bacteria to be antagonized in Petri's plates with cylinder sections of uniformly seeded confluent agar plate of the probiotic strain. The halo of growth inhibition around the cylinder section is measured.

Medium

Pathogen strains were grown in Oxoid medium. It was a standard commercial available Oxoid medium (Oxoid CM0359).

Incubation and Measurement

Pathogen strains were swabbed uniformly in plates containing Oxoid medium and grown to confluence in a $CO_2$ incubator at the appropriate temperatures and % $CO_2$ for the growth of each pathogen. Then, two 6 mm diameter cylinder sections of a uniformly seeded confluent agar plate of the probiotic strains to be tested were placed in contact with the pathogen seeded plate, confronting the pathogen seeded plate with the grown side of one of the cylinder sections and with the non-grown side of the other cylinder section and incubating overnight at 37° C.

Calculations

Next day, inhibition zones were measured by placing the agar plate over a flat rule. Growth inhibitory activity (GI) was then calculated by subtracting the cylinder diameter (CD) from the inhibition zone diameter (IZD) measured in centimeters and dividing this difference by 2, following the formula GI=(IZD−CD)/2. The inhibiting capabilities of the strains of the invention were compared to that of the commercial strain *L. reuteri*. The final inhibitory activity was calculated as mean of the GI values for the two above-mentioned cylinder sections for each strain.

Results

TABLE 2

Growth inhibitory activity (GI) of probiotic strains. Results expressed in cm; "n.i." denotes no inhibition

| Pathogen strain | Pediococcus pentosaceus CECT 833 | Bifidobacterium longum CECT 7894 | Lactobacillus reuteri |
|---|---|---|---|
| Gram negative bacteria | | | |
| *Escherichia coli* ATCC 10538 | 0.30 | >0.6 | n.i |
| *Enterobacter aerogenes* ATCC 13048 | 0.08 | >0.6 | 0.08 |
| *Klebsiella oxytoca* KT 801 | 0.54 | >0.6 | 0.13 |
| *Bacteroides vulgatus* ATCC 8482 | 0.21 | >0.6 | n.i |
| Gram positive bacteria | | | |
| *Enterococcus faecalis* ATCC 29212 | 0.35 | >0.6 | 0.08 |
| *Clostridium difficile* ATCC 9689 | 0.25 | 0.29 | 0.38 |

The strains displayed inhibitory activity against all the spectrum of pathogens studied. Therefore, the strains were effective inhibiting not only Gram positive but also Gram negative bacteria. This was not the case of *L. reuteri* which was inefficient inhibiting the growth of *E. coli* and *B. vulgatus*. This is of great interest as abnormal amounts of bacteria such as *E. coli* are commonly present in infants presenting excessive crying (De Weerth, C. et al. 2013 supra; Lehtonen, L. et al. "Intestinal Microflora in colicky and noncolicky infants: Bacterial Cultures and Gas-Liquid Chromatography", *Journal of pediatric Gastroenterology and Nutrition* 1994, vol. 19, pp. 310-314). It is also noteworthy that, in general, CECT 8330 and specially CECT 7894, were more efficient inhibiting the growth of almost all the pathogen bacteria compared to *L. reuteri*. Moreover, it is also relevant that both strains of invention provide protection against *Klebsiella* and *Clostridium*, which are also abundant in the intestine of infants presenting excessive crying (De Weerth, C. et al. 2013 supra; Lehtonen, L. et al. 1994 supra).

Example 3. No Production of Gas

Heterofermentative bacteria produce $CO_2$ and ethanol, as well as lactic acid, by glucose fermentation following the metabolic pathway:

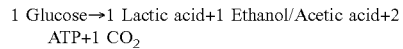

The production of $CO_2$ by the strains was determined. As it is shown in the formula, the production of $CO_2$ is also informative of the production of ethanol. The production of $CO_2$ was determined using the Durham Tubes technique, which is based on the incubation of the probiotic strain in heterofermentation broth in tubes containing smaller and inverted tubes inside, where the gas is accumulated when it is produced (Pilone, G. J., et al., "Characterization of wine lactic acid bacteria: single broth culture for tests of heterofermentation, mannitol from fructose, and ammonia from arginine" *Am J Enol Vitic* 1991, vol. 42, pp. 153-157).

The strains CECT 8330 and CECT 7894 did not produce gas. *L. reuteri* used as a control, did produce gas.

Example 4. Toxicity Assays

In contrast to bacteria from Bifodobacterium and *Lactobacillus* genus, *Pediococcus pentosaceus* is not commonly used as a probiotic for human consumption. Thus, although the probiotic strain CECT 8330 of the present invention belongs to a species which has QPS status additional toxicity assays were conducted to avoid any safety concern.

Given the high sensitivity of the babies due to their immature digestive tract, it was decided to develop a more appropriate model of acute toxicity using Wistar Han IGS Crl:WI neonatal rats (10 days after birth with a body weight range at the start of the experiment of 18-23 g), in order to ensure complete safety of the strains in infants.

Pregnant females were received at day 19th of gestation. After birth, litters were adjusted to 4 males and 4 females, mixing pups of all mothers in order to avoid maternal effects and achieve litters of equal size. Each lactating female were placed with 4 males and 4 females. Lactating females were fed with SAFE A03 diet and water ad libitum.

The experimental procedure comprised 4 groups: VEHICLE-translocation, VEHICLE-clinical signs, CECT 8330-translocation and CECT 8330-clinical signs.

Each group comprised a cage with a lactating female and a litter of 4 males and 4 females. CECT 8330 product was prepared daily at a final concentration of $0.5 \times 10^{10}$ cfu/ml formulation. VEHICLE group received water instead of probiotic. All neonatal rats were administered with the VEHICLE or CECT 8330 treatments for 5 days (from day 0 to day 4 of the study) by oral gavage with an orogastric cannula at a fixed volume of 5 ml/kg ($2.5 \times 10^{10}$ cfu/kg in the case CECT 8330). The oral route was chosen for the study because it is the intended route of administration in humans.

Observations during the experiment were: morbidity/mortality; body weight; clinical signs (appearance of the pup including hydration and body condition; response to a stimulus; natural activity—ability to wriggle if put in supine—and skin color).

Animals were euthanized after two different periods of time:
- Groups of "translocation" were euthanized on day 4 of experiment (last day of the 5-day treatment)
- Groups of "clinical signs" were euthanized on day 11th of the study (one week after the last oral dosing).

Pups were euthanized by decapitation and a necropsy was carried out, including the examination of the intact animal and all its surface tissues, followed by an internal examination of the thoracic and abdominal cavities. In the animals belonging to the "translocation" group, immediately after euthanasia, the liver of the animals were collected and maintained at 2-4° C. until bacterial translocation analysis. Approximately 5 mg of each liver sample was homogenized in 1 ml 0.01% gelatin PBS. One hundred µl from this homogenate were plated either on McConkey plates or MRS plates. Colonies were counted after incubation at 37° C. for 48 h.

No spontaneous mortality or toxicity-related clinical signs were observed during the study. No differences on body weight between control (vehicle) and CECT 8330 were detected and the behavior of all animals was normal. Moreover, no differences were observed between control and CECT 8330 groups in the number of animals showing translocation of either lactic acid bacteria or enterobacteria in the liver.

Example 5. Isolation of Strains

Fresh stools were collected from 0-9 year-old children and dissolved in PBS buffer (pH 7.4), aliquoted and plated on MRS supplemented with various antibiotic combinations. Strains were cultured under microaerophilic conditions (5% $CO_2$) at 37 or 30° C. Incubation time depended on the growth rate, but ran normally from 24 hours to 3 days. Gram staining was carried out in order to get a first identification. Once grown, isolated strains were stored by lyophilization in PBS 0.1× with 15% skim milk powder. The strains were grown on MRS agar supplemented with 10 µg/ml vancomycin. Microscopic examination revealed that *Bifidobacterium longum* CECT 7894 are Gram-positive bacilli, and *Pediococcus pentosaceus* CECT 8330 are Gram-positive coccus.

Genus and species identification was done by amplification of the 16S rRNA gene as previously described (Bosch, M. et al., Probiotic properties of *Lactobacillus plantarum* CECT 7315 and CECT 7316 isolated from faeces of healthy children. *Lett App. Microbiol*, 2012 vol. 54, pp. 240-6). SEQ ID NO: 1 corresponds to the 16S rRNA sequence of *Pediococcus pentosaceus* CECT 8330 and SEQ ID NO: 2 to the 16S rRNA sequence of *Bifidobacterium longum* CECT 7894.

Strain genotyping was performed by genomic digestion and pulsed-field gel electrophoresis (PFGE).

*Pediococcus pentosaceus* CECT 8330 was subjected to a previously described protocol (Rodas, A. M., et al., Polyphasic study of wine *Lactobacillus* strains: taxonomic implications. *Int J Syst Evol Microbiol*, 2005. 55(1): p. 197-207) with minor modifications. Since there were not commercial strains of *Pediococcus pentosaceus* available to use as controls, two commercial strains of *Pediococcus acidilactici* were included in the assay (1 and 2 in FIG. 1). Strains were grown on MRS agar plates and incubated at 37° C. 5% $CO_2$ for 18 h. Cells were harvested and washed 3 times in 8 ml PET (10 mM Tris pH 7.6, 1 M NaCl) then centrifuged at 6000 rpm 10 min. Pellets were resuspended in 700 ml lysis buffer (6 mM Tris, 1 M NaCl, 0.1 M EDTA, 0.5° A) SLS, 0.2% deoxycholic acid; 1 mg/ml lysozyme; 40 U/ml mutanolysin; 20 mg/ml RNase). An equal volume of 1.6% low melting point agarose (FMC BioProducts, Rockland, Me., USA) was added to the resuspended cells and solidification was allowed at 4° C. for 1 h. Inserts were transferred to 2 ml lysis buffer II (0.5 M EDTA pH 9.2, 1% N-lauryl sarcosine and 1 mg/ml pronase) and incubated at 50° C. for 48 h. Then inserts were washed at room temperature with TE buffer (10 mM Tris, 1 mM EDTA pH 8.0). Total DNA digestion was performed separately by Sma-I and Not-1 restriction enzymes (Roche Diagnostics). Pulsed-field gel electrophoresis was carried out using CHEF DRIII apparatus (BioRad Laboratories). Inserts were loaded in a 1° A) agarose gel (SeaKem ME agarose, FMC BioProducts, ME, USA). TABLE 3 describes electrophoresis conditions for each enzyme. DNA molecular weight markers were Lambda ladder PFG Marker and Low Range PFG Marker (New England Biolabs). After electrophoresis, gels were stained with ethidium bromide and UV using GelDoc System (Bio-Rad).

TABLE 3

| Electrophoresis conditions | | | | |
|---|---|---|---|---|
| Enzyme | Block | Initial Pulse (sec) | Final pulse (sec) | Time (hours) |
| Not-I | 1 | 2 | 25 | 18 |
| Sma-I | 1 | 0.5 | 5 | 16 |

*Bifidobacterium longum* CECT 7894 was characterized by PFGE using Xba I and Spe I as restriction enzymes as described by Briczinski, E. P. et al. "Technical note: a rapid pulsed-field gel electrophoresis method for analysis of bifidobacteria" *J. Dairy Sci.* 2006, vol. 89, pp 2424-2427. The resulting patterns were compared with those of *B. longum* CECT 4551.

Figure 2:
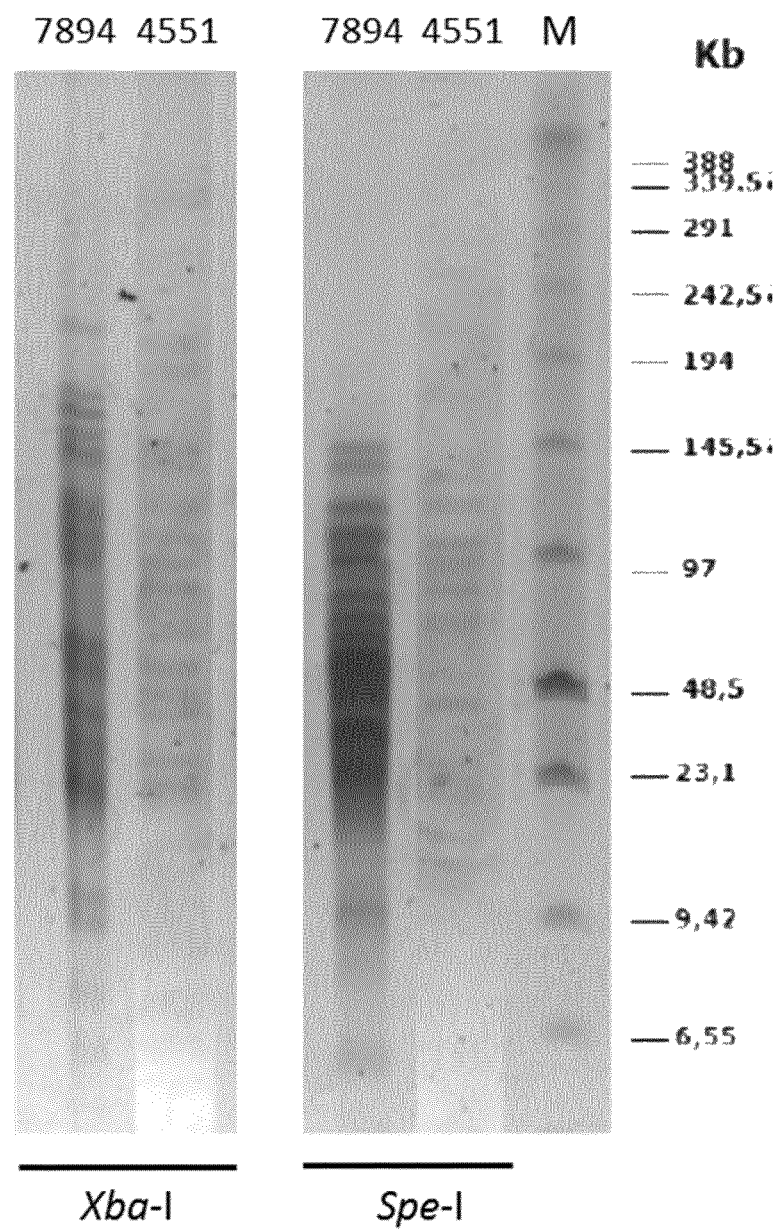
FIG. 2. Pulsed-field gel electrophoresis patterns of Xba-I (left) and Spe-I (right) restricted genomic DNA of, from left to right: *Bifidobacterium longum* CECT 7894 (7894), *Bifidobacterium longum* CECT 4551 (4551), and molecular marker (M).

The results are depicted in FIG. 1 and FIG. 2. Pulsed-field gel electrophoresis Not-I and Sma-I restriction patterns were different for the strain *Pediococcus pentosaceus* CECT 8330 and the commercial control strains belonging to *Pediococcus acidilactici* species (1 and 2). It was not possible to include *Pediococcus pentosaceus* strains as controls because they were not commercially available. PFGE allows distinguishing between strains of the same species, and thus can be used to uniquely identify a given bacterial strain within a bacterial species (Rodas, A. M., et al. 2005 supra).

Example 6. Preparation of an Oily Suspension

Four hundred ml of sunflower oil were introduced into a container provided with stirring means. Nine and a half g of colloidal silica were slowly added under stirring (150 rpm) to avoid the formation of lumps and agglomerations until complete homogenization. 13.3 g of *Pediococcus pentosaceus* CECT 8330 containing $5 \times 10^{12}$ cfus were added to the container under slow stirring (50 rpm) until complete dispersion. Then, 42.75 g of *Bifidobacterium longum* CECT 7894 containing $5 \times 10^{12}$ cfus were added to the container under slow stirring (50 rpm) until complete dispersion. The suspension was finally made up to 1000 ml with sunflower oil and stirred to homogenize the final suspension. The suspension was kept at room temperature.

Example 7. Clinical Study

Design of the Study

A pilot clinical trial was conducted to evaluate the efficacy and safety of the probiotic formula combining *P. pentosaceus* CECT 8330 and *B. longum* CECT 7894. The study was designed as a prospective double-blind, placebo-controlled, randomized clinical trial with two parallel arms which involved a total number of 8 participating centers from Catalonia (Spain). The study protocol was approved by the Ethical Committees from IDIAP Jordi Gol (Barcelona, Spain) and from Fundació Unió Catalana d'Hospitals (Barcelona, Spain) in compliance with the Helsinki Declaration.

Healthy term infants of both sexes meeting all of the following inclusion criteria were recruited: from 21 to 120 days old; minimum birth weight of 2.5 Kg; either breastfed or feed with infant formula (hydrolyzed or initiation formula); excessive crying and fussing according to the definition "intense, persistent and inconsolable crying, problematic for the normal family unit functioning, which implies at least 60 minutes per day in 3 or more episodes in 3 or more days observed during at least 1 week, previously ruling out an organic etiology, like intestinal intussusception or others". Exclusion criteria were: Pre-term infants (born before 37 weeks); chronic illness; history of gastrointestinal disorders (not related to colic); immunosuppressed infants; previous or expected surgical intervention; having taken probiotics or antibiotics one week before the enrollment; infants whose parents or representatives were not able to appropriately follow the study requirements. Subjects were randomly assigned to either probiotic treatment group or placebo group. The treatment consisted in a composition as described in EXAMPLE 6. Placebo consisted in the same oily suspension without probiotic. Compositions were administered 30 minutes before feeding (5 drops/day) for 14 days. During the study, parents were asked to fill questionnaires recording the adhesion to the treatment, crying evolutions and adverse effects.

Data analysis was performed with IBM® SPSS Statistic v20 for Windows and results expressed as averages and standard errors. Average reduction in daily crying time during clinical trial was calculated as the difference between the average of the total number of minutes of crying per day during the last 3 days of the study (days 12, 13 and 14) and the average of total number of minutes per days during the first 3 days of study (days 1, 2 and 3). Average reduction in the duration of each episode was calculated as the difference between the average of the number of minutes lasting each episode during the last 3 days of the study (days 12, 13 and 14) and the average of minutes lasting each episode during the first 3 days of study (days 1, 2 and 3).

Results

Figure 3:
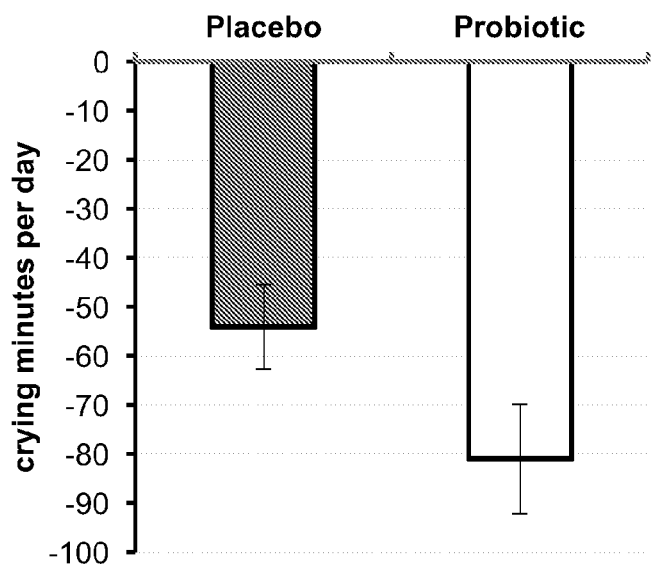
FIG. 3. Reduction in average daily crying time and in duration of each episode. A) Reduction in average daily crying time (total minutes cried per day). B) Reduction in average duration of each episode (minutes per episode). Results expressed as means±standard error of the mean (SEM) for n=9 in placebo group and n=11 in probiotic formula group.
Figure 3:
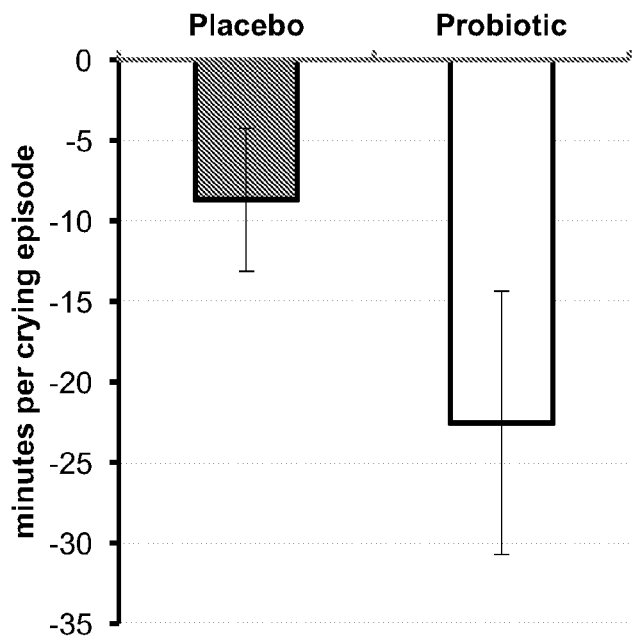

At the beginning of the clinical trial it was confirmed that n=9 infants belonging to the placebo group and n=11 belonging to the probiotic formula group met the proposed definition of crying time and were therefore allowed to continue the study. The average crying time of this population at the beginning of the study ranged from 60 to 240 minutes. During the study, both placebo and probiotic formula were well tolerated and no adverse effects related to supplementation were observed. Moreover, as shown in FIG. 3, crying time was reduced in both placebo and probiotic group during the study. However, probiotic consumption caused a higher reduction in average crying time. A similar trend was observed for the duration of each episode.

The clinical effect observed supports the probiotic properties observed in vitro. These results are of relevant interest as this study presents some strength compared to other studies where probiotics have been used for treating colic. For instance, the study included both breastfed and formula-fed infants, which is of relevant interest as current probiotic formulas have failed to display any improvement in formula-fed sub-populations. Moreover, participating infants were recruited based on clinical definition of infant colic more realistic according to daily clinical practice and the treatment period (14 days) was shorter than that of many other clinical trials (21-28 days).

BIBLIOGRAPHIC REFERENCES

Andreoletti, O. et al. "The maintenance of the list of QPS microorganisms intentionally added to food or feed. Question no: EFSA-Q-2008-006", *The EFSA Journal* 2008, vol. 923, pp. 1-48.

Bosch, M. et al., "Probiotic properties of *Lactobacillus plantarum* CECT 7315 and CECT 7316 isolated from faeces of healthy children". *Lett App. Microbiol,* 2012. 54, 240-6

Briczinski, E. P. et al. "Technical note: a rapid pulsed-field gel electrophoresis method for analysis of bifidobacteria" *J. Dairy Sci.* 2006, vol. 89, pp. 2424-2427.

De Weerth, C. et al. "Intestinal Microbiota of Infants with colic: Development and specific signatures" *Pediatrics* 2013, vol. 131, Issue 2, e550-e558.

Dupont, C. et al. "A-Lactalbumin-Enriched and Probiotic-Supplemented Infant Formula in Infants with Colic: Growth and Gastrointestinal Tolerance." *European Journal of Clinical Nutrition.* 2010, vol. 64, Issue 7, pp. 765-767.

Igarashi T. "Study of the relationship between changes in lactic acid bacterial cell components and stimulation of IL-12 production under salt-stressed conditions", *Bioscience, Biotechnology and Biochemistry* 2010, vol. 74, pp. 2171-2175

Jonganurakkun, B. et al. "*Pediococcus pentosaceus* NB-17 for probiotic use", *Journal of Bioscience and Bioengineering* 2008 vol. 106, Issue 1, pp. 69-73

Lehtonen, L. et al. "Intestinal Microflora in colicky and noncolicky infants: Bacterial Cultures and Gas-Liquid Chromatography", Journal of pediatric Gastroenterology and Nutrition 1994, vol. 19, pp. 310-314.

Mentula, S. et al. "Microbial composition and fecal fermentation end products from colicky infants—A probiotic supplementation pilot", *Microbial Ecology in Health and Disease,* 2008, vol. 20, no. 1, pp. 37-47.

Roos, S. et al. "454 Pyrosequencing Analysis on Faecal Samples from a Randomized DBPC Trial of Colicky Infants Treated with *Lactobacillus reuteri* DSM 17938", *PLoS ONE* 2013, vol. 8, no. 2, e56710 1-5

Savino, F. et al. "*Lactobacillus reuteri* (American Type Culture Collection Strain 55730) Versus Simethicone in the Treatment of Infantile Colic: A Prospective Randomized Study" *Pediatrics* 2007, vol. 119, Issue 1, e124-e130.

Savino, F. et al. "*Lactobacillus reuteri* DSM 17938 in Infantile Colic: A Randomized, Double-Blind, Placebo-Controlled Trial." *Pediatrics* 2010, vol 126, Issue 3, e526-e533.

Szajewska, H. et al. "*Lactobacillus reuteri* DSM 17938 for the Management of Infantile Colic in Breastfed Infants: A Randomized, Double-Blind, Placebo-Controlled Trial", *Journal of Pediatrics* 2012, vol. 162, Issue 2, pp. 257-262.

Vitali, B. et al. "Novel probiotic candidates for humans isolated from raw fruits and vegetables", *Food Microbiology* 2012, vol. 31, Issue 1, pp. 116-125

Pilone, G. J., et al., "Characterization of wine lactic acid bacteria: single broth culture for tests of heterofermentation, mannitol from fructose, and ammonia from arginine" *Am J Enol Vitic* 1991, vol. 42, pp. 153-157

WO2007142596

The invention claimed is:

1. A method for screening and isolating novel *Pediococcus pentosaceus* cells, comprising the following steps:
   (I) assaying new *Pediococcus pentosaceus* cells from a pool of *Pediococcus pentosaceus* cells for their ability to induce the production of interleukin-10 by the following steps;
      (a) differentiating THP-1 monocytes into macrophages by growing the THP-1 monocyte cell line obtained from the cell collection of the Public Health England, catalogue number 88081201, in Roswell Park Memorial Institute (RPMI) 1640 medium with 10% Fetal Bovine Serum (FBS), and with phorbol 12-myristate 13-acetate (PMA) to a final concentration of 0.16 µM;
      (b) growing the THP-1 macrophages in RPMI 1640 medium with 10% FBS in 24-wells ELISA plates to a final concentration of $10^6$ macrophages/well;
      (c) incubating for 2.5 hours the THP-1 macrophages with lipopolysaccharide (LPS) at a final concentration of 10 ng/ml, and washing the THP-1 macrophages with Dulbecco's Phosphate Buffered Saline medium (D-PBS);
      (d) getting a culture of *Pediococcus pentosaceus* cells ready by having grown it overnight in Man, Rogosa and Sharpe medium (MRS) at 37° C. in a 5% $CO_2$ atmosphere;
      (e) adding to each ELISA-well 500 µl of RPMI 1640 medium with 10% FBS and an appropriate amount of a dilution of *Pediococcus pentosaceus* cells to obtain a final ratio of 25:1, i.e. $2.5\times10^7$ cfu of *Pediococcus pentosaceus* cells: $10^6$ THP-1 macrophages;
      (f) incubating the THP-1 macrophages with the *Pediococcus pentosaceus* cells for 2.5 hours at 37° C. or without the *Pediococcus pentosaceus* cells in the same conditions as negative control;
      (g) washing the THP-1 macrophages with D-PBS medium to remove the *Pediococcus pentosaceus* cells, subsequently adding to the THP-1 macrophages RPMI 1640 medium with 10% FBS supplemented with 50 µg/ml gentamicin, 10 µg/ml ampicillin and 12 µg/ml chloramphenicol, incubating at 37° C. at 5-7% $CO_2$, and taking aliquots at 5 and 24 hours;
      (h) centrifuging the aliquots and assaying the supernatants for interleukin-10 quantification by flow cytometry; and
      (i) calculating the normalized increase of interleukin-10 concentration, with the formula $(IL10_{24\ h} - IL10_{5\ h})/IL10_{5\ h}$; wherein $IL10_{5\ h}$ and $IL10_{24\ h}$ is the concentration of interleukin-10 in pg/ml at 5 and 24 hours, respectively;
   (II) selecting and isolating the new *Pediococcus pentosaceus* cells from the pool that induces a production of interleukin-10, expressed as normalized increase, higher than the production of interleukin-10 by the negative control, wherein said normalized increase is determined as defined in step(I).

2. A method for reducing daily crying time and/or duration of crying episodes in an infant in need thereof, wherein said reduction of time and/or duration of said crying is associated with infant colic, comprising administering to said infant an amount of a bacterial composition which comprises from $10^4$ to $10^{12}$ cfu/g of *Pediococcus pentosaceus* viable cells, which induce the production of interleukin-10, wherein *Pediococcus pentosaceus* is the *Pediococcus pentosaceus* deposited in the Spanish Type Culture Collection under accession number CECT 8330.

3. The method of claim 2, wherein said composition further comprises *Bifidobacterium longum*.

4. The method of claim 3, wherein the *Bifidobacterium longum* is the *Bifidobacterium longum* deposited in the Spanish Type Culture Collection under the accession number CECT 7894.

5. The method according to claim 2, wherein said infants have an age from three weeks to twelve months.

6. The method according to claim 2, wherein said infants cry at least 60 minutes per day in three or more episodes for at least one week.

7. The method according to claim 2, wherein said infants cry at least 3 hours per day for at least one week.

8. The method according to claim 2, wherein said composition is administered in an amount sufficient to antagonize Gram positive and Gram negative intestinal bacteria.

9. A method for reducing daily crying time and/or duration of crying episodes in an infant in need thereof, wherein said reduction of time and/or duration of said crying is associated with infant colic, comprising administering to said infant an amount of a probiotic bacterial composition which comprises from $10^4$ to $10^{12}$ cfu/g of *Pediococcus pentosaceus* cells which: (a) induce the production of interleukin-10; (b) antagonize Gram positive and Gram negative intestinal bacteria, wherein said Gram negative intestinal bacteria is selected from the group consisting of *Escherichia coli, Enterobacter aerogenes, Klebsiella oxytoca* and *Bacteroides vulgatus*, effective for reducing the time and/or duration of crying in said infant and wherein the *Pediococcus pentosaceus* cells; (c) have probiotic properties that survive the passage of the gastrointestinal tract, colonize the intestinal tract and grow in industrial medium, (d) do not produce gas and (e) have a 16S nucleic acid sequence set forth in SEQ ID NO: 1.

10. The method according to claim 9, wherein said *Pediococcus pentosaceus* cells survive after lysozyme, hydrogen peroxide, acidic environment or bile salt treatment.

11. The method according to claim 9, wherein said infants have an age from three weeks to twelve months.

12. The method according to claim 9, wherein said infants cry at least 60 minutes per day in three or more episodes for at least one week.

13. The method according to claim 9, wherein said infants cry at least 3 hours per day for at least one week.

14. The method according to claim 13, wherein the Gram positive bacteria comprise bacteria selected from the group consisting of *Clostridium difficile* and *Enterococcus faecalis*.

15. The method according to claim 9, wherein said composition further comprises *Bifidobacterium longum*.

16. A method for reducing daily crying time and/or duration of crying episodes in an infant in need thereof, wherein said reduction of time and/or duration of said crying is associated with infant colic, comprising administering to said infant an amount of a probiotic bacterial composition which comprises (a) from $10^4$ to $10^{12}$ cfu/g of *Pediococcus pentosaceus* cells and (b) *Bifidobacterium longum* effective to induce IL-10 production and antagonize Gram positive and Gram negative intestinal bacteria, wherein said Gram negative intestinal bacteria is selected from the group consisting of *Escherichia coli, Enterobacter aerogenes, Klebsiella oxytoca* and *Bacteroides vulgatus*.

* * * * *